United States Patent [19]

Cognion et al.

[11] 4,323,515

[45] Apr. 6, 1982

[54] PROCESS FOR THE PREPARATION OF ORGANIC ISOCYANATES FROM NITRO DERIVATIVES

[75] Inventors: Jean-Marie Cognion, Saint Genis Laval; Jacques Kervennal, Lyons, both of France

[73] Assignee: P C U K Produits Chimiques Ugine Kuhlmann, Courbevoie, France

[21] Appl. No.: 77,521

[22] Filed: Sep. 20, 1979

[30] Foreign Application Priority Data

May 15, 1979 [FR] France ................................. 79 12272

[51] Int. Cl.$^3$ .......................................... C07C 119/048
[52] U.S. Cl. .................................................. 260/453 P
[58] Field of Search ..................................... 260/453 P

[56] References Cited

U.S. PATENT DOCUMENTS

| | | | |
|---|---|---|---|
| 2,966,453 | 12/1960 | Gleim et al. ...................... | 260/453 P |
| 3,576,835 | 4/1971 | Smith et al. ............................... | 546/9 |
| 4,070,307 | 1/1978 | Daglas et al. .................... | 260/453 P |
| 4,072,630 | 2/1978 | Daglas et al. .................... | 260/453 P |

FOREIGN PATENT DOCUMENTS

| | | | |
|---|---|---|---|
| 2507671 | 2/1975 | Fed. Rep. of Germany ... | 260/453 P |
| 2014174 | 4/1970 | France .............................. | 260/453 P |
| 2032277 | 11/1970 | France .............................. | 260/453 P |
| 2155242 | 4/1973 | France .............................. | 260/453 P |

OTHER PUBLICATIONS

Grignard, Traite' de Chimie. Organique, pp. 203, 212, 214, 215, 218, 220, 221–223, Tome XIX.

*Primary Examiner*—John M. Ford
*Assistant Examiner*—Robert C. Whittenbaugh
*Attorney, Agent, or Firm*—Beveridge, Degrandi and Kline

[57] ABSTRACT

A process for the synthesis of aromatic isocyanates by the reduction of aromatic derivatives with carbon monoxide in the presence of catalysts consisting of metal complexes of porphyrins. In one embodiment, the metallic porphyrin is synthesized in situ from a porphryin and a metal or a metal derivative.

39 Claims, No Drawings

PROCESS FOR THE PREPARATION OF ORGANIC ISOCYANATES FROM NITRO DERIVATIVES

The present invention relates to a process for the synthesis of organic isocyanates from nitro compounds and more especially, a process for the preparation in the liquid phase of aromatic isocyanates by reaction between aromatic nitro derivatives and carbon monoxide in the presence of new catalysts consisting of the metal complexes of the porphyrins.

The aromatic isocyanates are organic intermediates of great interest. Two of these are particularly important industrially, namely, toluene 2,4-diisocyanate and diphenylmethane 4,4'-diisocyanate, which are used in the synthesis of polyurethanes. The industrial processes for the preparation of these products all bring in the reaction of phosgene with an amine proceeding from the catalytic hydrogenation of a nitro derivative. The disadvantages of these processes are many: they necessitate the synthesis and the handling of phosgene, a very dangerous product; they produce hydrochloric acid in large quantities, which requires the costly introduction and maintenance of a special plant or workroom for the electrolysis of this acid so as to recycle the chlorine.

The interest which a process avoiding the use of phosgene would have is evident and several patents have claimed catalytic compositions which enable the synthesis of isocyanates, at increased temperature and pressure, to be effected by the reaction of an organic nitro compound with carbon monoxide. Thus, French Pat. No. 1,600,529 filed on Dec. 11, 1968, which corresponds to U.S. Pat. No. 3,576,835, describes the use as catalyst of a noble metal halide in the presence of an amino base of aromatic character; German Pat. No. 1,910,303, filed on February 28, 1969, which corresponds to U.S. Pat. No. 3,626,027, claims catalysts formed from halides or oxides of Ru, Rh, Pd, Os, Ir, Pt, and a hetero-aromatic sulfur compound in the possible presence of an oxide of Cr, Mo, Nb, W, V; French Pat. No. 1,567,321, filed on Apr. 5, 1968, which corresponds to U.S. Pat. No. 3,523,962, describes the use of a catalytic system formed from a noble metal halide and an organic phosphorus compound, for example, a triarylphosphine or a phosphite. French Pat. No. 72.30141 (2,155,242), filed on Aug. 24, 1972, which corresponds to U.S. Pat. No. 3,776,935, claims catalytic systems consisting of one or more palladium and/or rhodium halides, one or more heteroatomic nitrogenous bases and a co-catalyst formed from one or more iron borates; in French Pat. No. 71.47284 (2,120,110), which corresponds to U.S. Pat. No. 3,719,699, the catalytic formulation comprises, in addition to a palladium halide and heteroatomic nitrogenous bases, a co-catalyst consisting of one or more iron and/or manganese molybdates. All of these systems produce isocyanates from nitro compounds with variable selectivities and productivities.

The present inventors have found that the direct reduction reaction of aromatic nitro derivatives to isocyanates by carbon monoxide is effected with good yields by means of new catalysts constituted by metal complexes of the porphyrins. These complexes have a good chemical and thermal stability and do not lead, like the majority of the catalyst systems described above, to the formation of azo derivatives.

According to the present invention, the nitro compounds are placed in contact with the carbon monoxide at elevated temperature and pressure in the presence of one or more metal porphyrins. It is possible to operate in the presence of an organic solvent, by a discontinuous technique in an apparatus of the autoclave type or by a continuous technique which enables the isocyanate produced to be eliminated as it is formed. The reaction equation may be written according to the following scheme:

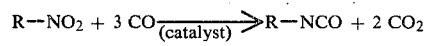

The process according to the present invention is applicable to aromatic compounds carrying one or more nitro groups attached to a carbon atom of an aromatic nucleus, these compounds being represented by the general formula:

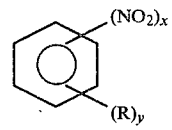

in which $x=1$ or 2 and $y=0$, 1, 2 or 3, R being a group of atoms or an atom attached to the aromatic nucleus and which may represent an alkyl group having from 1 to 10 carbon atoms, a halogen atom, chlorine or bromine, for example, or an alkoxy group OR' in which R' is an alkyl radical having from 1 to 10 carbon atoms. Examples, which are not restrictive, of aromatic compounds with one or more nitro functions utilizable according to the present invention are nitrobenzene, orthonitrotoluene, paranitrotoluene, 1,2-dinitrobenzene, 1,3-dinitro-benzene, 1,4-dinitro-benzene, 1,2,4-trinitrobenzene, 1,3,5-trinitro-benzene, 2,4-dinitro-toluene, 2,6-dinitrotoluene, 1-methoxy-2,4-dinitro-benzene, 1-chloro-2-nitro-benzene and 1-chloro-2,4-dinitro-benzene.

The metallic porphyrins employed as catalysts are obtained by reacting a metal salt or a metal complex on a previously prepared porphyrin ligand, according to the methods of synthesis cited and described in the works of K. M. Smith, *Porphyrins and Metalloporphyrins*, Elsevier (1975), and D. Dolphin, *The Porphyrins*, Academic Press (1978).

The porphyrins used to catalyze the reaction may possibly carry different substituents, for example a linear or branched alkyl group containing from 1 to 10 carbon atoms or an aromatic group containing from 6 to 12 carbon atoms. Tetraphenylporphyrin and octaethylporphyrin are preferably used.

The metals which are particularly suitable for the present invention are the metals of Groups VIII and $I_B$ of the Periodic Classification of the Elements and especially the following: iron, cobalt, nickel, ruthenium, rhodium, palladium, iridium, copper and silver.

The concentration of the catalyst expressed as the ratio of the number of gram atoms of the metal and the number of nitro groups to be converted can vary between $10^{-4}$ and 1 preferably between $5.10^{-3}$ and $10^{-1}$.

The reaction may be effected in the absence of solvent, but the presence of a solvent chemically inert in the reaction generally favors the selectivity to isocyanate. The solvents preferably used are saturated aliphatic or aromatic hydrocarbons such as hexane, heptane, decane, decalin, benzene, toluene or xylene and aromatic halides such as chlorobenzene and dichlorobenzenes. The proportion of solvent is not critical, but it is general to use solutions containing 5% to 50% by weight of the nitro derivative in the solvent.

The metallo-porphyrins may be used as such as catalysts, but they may also be deposited on a support in order to disperse the catalyst and facilitate its recovery. Among possible supports may be mentioned silicas, aluminas, silica-aluminas, activated carbons, magnesia, zirconia, or silicon carbide.

The reaction temperatures are between 100° and 500° C. and more particularly from 150° to 300° C. according to the nature and stability of the reagents used under the operating conditions.

The reaction pressures are from 20 to 500 bars, preferably from 150 to 350 bars, and must be sufficient to maintain a considerable fraction of the reagents in the liquid phase and to introduce a total amount of carbon monoxide corresponding to a molar ratio:

$$\frac{CO}{NO_2 \text{ groups}}$$

generally from 3 to 100 and preferably from 10 to 65.

According to another mode for carrying out the present invention, the prior preparation of metalloporphyrins can be avoided, the latter being synthesized in situ from a porphyrin and a metal or a metal derivative.

According to this embodiment of the invention the nitro compound, the reaction solvent, the porphyrin and the metal derivative usually in the form of metal powder, oxide or a salt, preferably the chloride or acetate, are introduced into the reactor. After scavenging with nitrogen, the reactor is placed under carbon monoxide pressure and heated to the reaction temperature. When the reaction is completed, the entire mixture is recovered in which may be verified by visible spectroscopy the presence of the metalloporphyrin formed in situ. The solvent and the isocyanate formed are distilled and a residue is obtained containing the complex, which may be recycled as such or previously purified, for example by passage over a column filled with alumina, using chloroform as the solvent of elution or using an extraction technique with a solvent such as ether. The metalloporphyrin can thus be obtained with a yield of 98% with respect to the metal introduced. The recycling of the catalyst is effected without loss of activity.

The concentration of metal introduced expressed by the relation between the number of gram-atoms of the metal and the number of nitro groups to be converted may vary between $10^{-4}$ and 1 and preferably between $5 \cdot 10^{-3}$ and $10^{-1}$.

The content of porphyrin introduced may vary between $10^{-1}$ and 10 moles per gram-atom of metal, but is preferred to use the stoichiometric quantity necessary to form the complex.

This embodiment of the present invention enables the operative conditions of this isocyanate synthesis to be simplified by avoiding the initial preparation of the metalloporphyrin complexes, these being formed in situ during the reaction. The process for the synthesis of the aromatic isocyanates is thus characterized in that the aromatic nitro derivative is reacted with the carbon monoxide in the presence of a catalyst consisting of metallic porphyrin synthesised in situ from a porphyrin and a metal or a metal derivative.

If desired, this embodiment permits not only the manufacture of isocyanates, but also the formation of the metalloporphyrin complexes under pressure of carbon monoxide in the presence of a nitro derivative, these complexes being able to be recovered for other uses.

The tests described in the following examples have been carried out discontinuously in a 500 ml stainless steel autoclave, provided with a magnetic agitation device, operable under pressures going up to 500 bars and temperatures of 300° C. The reactor, charged with the various reagents in solution, is then scavenged with nitrogen before being put under pressure of carbon monoxide at ambient temperature. The autoclave is isolated and is then heated at the selected temperature and the progress of the reaction is controlled by recording the pressure. The first tests were effected on mononitro aromatic derivatives. After reaction, the contents of isocyanates are evaluated by chemical dosage with dibutylamine and those of residual nitro derivatives and possibly azo derivatives by vapor phase chromatography.

In the following examples, to which the invention is not restricted, the results indicated are subject to the following definitions:

O.C.R. = Overall conversion rate =
$$\frac{\text{Number of moles of nitro derivative converted}}{\text{Number of moles of nitro derivative introduced}} \times 100$$

Selectivity for isocyanates =
$$\frac{\text{Number of moles of isocyanate formed}}{\text{Number of moles of nitro derivative converted}} \times 100$$

Yield of isocyanate =
$$\frac{\text{Number of moles of isocyanate formed}}{\text{Number of moles of nitro derivative introduced}} \times 100$$

EXAMPLE 1

Palladium tetraphenylporphyrin is prepared according to the method of operation described by D. W. Thomas and A. E. Martell, J. Amer. Chem. Soc., Vol. 81, p. 5111 (1959). 10 grams of purified tetraphenylporphyrin and 7.7 grams of palladium chloride are placed in 385 ml of acetic acid. The mixture is refluxed for 10 minutes, then 23 grams of sodium acetate are added and the mixture is refluxed for an hour and then a further 23 grams of sodium acetate are added. After 2 additional hours under reflux, the mixture is allowed to cool and poured into 800 ml of water. The precipitate is obtained by filtration, washed with water and, after drying, 12.3 grams of the Pd complex is obtained.

The chemical analysis indicates a content of 14.8% of palladium and a content of chlorine less than 0.5%. 2.0 grams of palladium porphyrin and 30 grams of nitrobenzene are charged into the autoclave previously described and the total volume is completed to 100 ml with orthodichlorobenzene. A stream of nitrogen is passed in at atmospheric pressure, then it is compressed with carbon monoxide until the pressure reaches 200 bars at 20° C. The autoclave is isolated and heated to 230° C., which brings the pressure of 340 bars. The mixture is allowed to react for 7 hours while maintaining it under agitation, then allowed to cool and analyzed. The O.C.R. of the nitrobenzene is 25.4% and the selectivity to phenylisocyanate is 94.8%. No azobenzene is formed.

EXAMPLE 2

Into the autoclave previously described, 2 grams of palladium tetraphenylporphyrin and 30 grams of nitrobenzene are introduced and the total volume adjusted to 100 ml by means of orthodichlorobenzene. The reactor is closed and after scavenging with nitrogen, carbon monoxide is introduced until the pressure reaches 200 bars at 20° C. The autoclave is isolated and while maintaining an agitation is heated at 235° C. for 3 hours, then at 240° C. for 4 hours, 30 minutes. After cooling, the mixture is analyzed. The O.C.R. of the nitrobenzene is 94.7% and the selectivity for phenylisocyanate is 60.2%. No azobenzene is formed.

EXAMPLE 3

1.4 grams of palladium tetraphenylporphyrin are introduced into the autoclave previously described. 20 grams of nitrobenzene are added and the total volume is brought to 200 ml by means of orthodichlorobenzene. It is scavenged with nitrogen and carbon monoxide is introduced until a pressure of 200 bars at 20° C. is reached. The autoclave is isolated, and while maintaining in agitation it is heated at 240° C. for 4 hours, then at 250° C. for 4 hours. After cooling, analysis shows that the O.C.R. for the nitrobenzene is 100% and the selectivity for phenylisocyanate is 69.3%. There is no trace of azobenzene.

EXAMPLE 4

0.7 grams of palladium tetraphenylporphyrin, and 10 grams of nitrobenzene are placed in the autoclave previously described and the total volume is brought to 100 ml by addition of orthodichlorobenzene. The autoclave is closed and, after scavenging with nitrogen, carbon monoxide is introduced until the pressure reaches 200 bars at 20° C. After having isolated the reactor and started the agitation, it is heated to 250° C. for 1 hour, then at 243° C. for another hour. After cooling, the analysis indicates that the O.C.R. of the nitrobenzene is 100% and the selectivity for phenylisocyanate is 69.3%. There is no formation of azobenzene.

EXAMPLE 5

0.7 gram of palladium tetraphenylporphyrin and 10 grams of nitrobenzene are introduced into the autoclave previously described and the total volume is brought to 100 ml by addition of orthodichlorobenzene. It is scavenged with nitrogen, then carbon monoxide is introduced until the manometer indicates a pressure of 200 bars at ordinary ambient temperature. The autoclave is isolated, the agitation is started, and it is heated at 240° C. for 2 hours and at 235° C. for an additional hour. After cooling, the mixture is analyzed. For an O.C.R. of 100% of nitrobenzene, the selectivity for phenylisocyanate is 81.2%. There is no trace of azobenzene.

EXAMPLE 6

0.7 gram of palladium tetraphenylporphyrin and 10 grams of orthonitrotoluene are placed in the autoclave previously described and the total volume is brought to 100 ml with orthodichlorobenzene. After scavenging with nitrogen, the carbon monoxide is introduced until the pressure attains 200 bars at 20° C. The autoclave is isolated, agitation is started, and it is heated at 240° C. for 3 hours, then at 245° C. for 2 hours, 30 minutes, and finally at 250° C. for 2 hours. After cooling, analysis indicates that the O.C.R. of the orthonitrotoluene is 17.5% and the selectivity for orthotoluene isocyanate is 55%.

EXAMPLE 7

Palladium tetraphenylporphyrin is prepared according to the experimental method described by A. D. Adler, F. R. Longo, F. Kampas and J. Kim, J. Inorg. Nucl. Chem. Vol. 32, p. 2443 (1970). To 300 ml of boiling dimethylformamide are added 3 g of tetraphenylporphyrin. After dissolution is effected, 0.9 g of palladium chloride is added. The mixture is refluxed for 10 minutes, then cooled in an ice bath and poured into 300 ml of water. The precipitate is filtered, washed with water and dried.

Chemical analysis indicates a palladium content of 14.3% and a chlorine content of 2.4%. 10 grams of nitrobenzene and 0.7 gram of palladium porphyrin are charged into the autoclave and the total volume is brought to 100 ml with orthodichlorobenzene. The reactor is closed, scavenged with a stream of nitrogen, and filled with carbon monoxide until the pressure reaches 200 bars at 20° C. The autoclave is isolated and, while maintaining agitation, is heated to 240° C. for 3 hours. The reaction mixture is then allowed to cool and analyzed. The O.C.R. of nitrobenzene is 100% and the selectivity to phenylisocyanate is 60.2%. No azobenzene is detected.

EXAMPLE 8

Iron tetraphenylporphyrin is prepared according to the experimental method described in Example 7. In 200 ml of boiling dimethylformamide 2 grams of tetraphenylporphyrin are dissolved; then 1.6 gram of $FeCl_2.4H_2O$ is added. The mixture is refluxed for 20 minutes, then allowed to cool in an ice bath and the complex is precipitated by adding 200 ml of deoxygenated water. This precipitate is filtered under nitrogen, washed with water and dried under vacuum.

2.3 grams of the iron complex are obtained which are divided in two parts: one is kept under vacuum whereas the second is maintained in contact with air.

0.7 gram of the first sample is introduced into the autoclave previously described. 10 grams of nitrobenzene are added and the total volume is brought to 100 ml with orthodichlorobenzene The reactor is scavenged with a stream of nitrogen and carbon monoxide is introduced until the pressure reaches 200 bars at 20° C. The reactor is isolated and, while maintaining agitation, heated to 240° C. for 6 hours, 30 minutes. After cooling, the mixture is analyzed. The O.C.R. of nitrobenzene is 88.1% and the selectivity to phenylisocyanate is 80.6%. No azobenzene is detected.

EXAMPLE 9

10 grams of nitrobenzene are introduced into the autoclave with 0.7 gram of iron tetraphenylporphyrin, the synthesis of which has been described in Example 8 and which has been in contact with air. The total volume is brought to 100 ml with orthodichlorobenzene. The same experimental conditions as described in Example 8 are applied. Analysis shows an O.C.R. of nitrobenzene of 92.2% and a selectivity to phenylisocyanate of 59.7%. No azobenzene is detected.

EXAMPLE 10

10 g of nitrobenzene, 0.6 g pf tetraphenylporphyrin and 0.1 g of palladium black are charged into the autoclave. The total volume is brought to 100 ml by means of orthodichlorobenzene and then the autoclave is closed. After scavenging with nitrogen, 200 bars of carbon monoxide are introduced and then the autoclave is heated to 240° C. The mixture is allowed to react for 8 hours while stirring is maintained, then cooled and analyzed. The optical absorption spectrum in the visible light, effected on a dilution in chloroform of the crude reaction mixture, shows that the palladium porphyrin has formed well in the autoclave; indeed, a spectrum is obtained with two characteristic bands of a metalloporphyrin with an absorption band at 524 nm and an intense band, the "Soret band", at 418 nm. The tetraphenylporphyrin itself has a different spectrum with absorption maxima at 645 nm, 592 nm, 550 nm, 513 nm and the "Soret band" at 419 nm.

The O.C.R. of the nitrobenzene is 100% and the selectivity to phenylisocyanate is 76.5%. No azobenzene is detected.

EXAMPLE 11

After distillation of the phenylisocyanate formed and the orthodichlorobenzene contained in the reaction mixture of Example 10, the residue obtained, which contains the palladium tetraphylporphyrin formed, is placed in the autoclave. The 7 g of nitrobenzene are introduced and the total volume is brought to 100 ml by means of orthodichlorobenzene. The autoclave is scavenged with nitrogen and 200 bars of CO are introduced. The autoclave is isolated and while stirring is maintained, it is heated at 240° C. for 3 hours. After cooling, the mixture is analyzed. The O.C.R. of the nitrobenzene is 94.7% and the selectivity to phenylisocyanate is 53%. No azobenzene is detected.

EXAMPLE 12

The operation is as in Example 10, but the quantities of palladium black and tetraphenylporphyrin are doubled. After reaction has taken place, the phenylisocyanate and the solvent are distilled and the residue, containing the palladium porphyrin, is dissolved in the chloroform. The solution is then subjected to chromatography in a column filled with neutral alumina and eluting with chloroform. A deep red solution is thus collected with a slowly evaporated to dryness. The precipitate obtained is identified as being of pure palladium tetraphenylporphyrin by visible spectroscopy, mass spectroscopy and microanalysis. The yield of complex is 91%.

0.7 g of this complex and 10 g of nitrobenzene are charged into the autoclave and the charge is made up to a total volume of 100 ml by orthodichlorobenzene. After scavenging with nitrogen, 200 bars of CO are introduced, the autoclave is isolated and taken to 240° C. with stirring for 6 hours. After cooling, the mixture is analyzed. The O.C.R. of the nitrobenzene is 95.3% and the selectivity for phenylisocyanate is 62%. The catalyst is treated in the same way as in the previous examples which enables it to be verified that the palladium porphyrin formed is not degraded; it is again obtained with a yield of 90% with respect to the complex introduced.

EXAMPLE 13

10 g of nitrobenzene, 0.6 g of tetraphenylporphyrin and 0.1 g of palladium black are placed in the autoclave and the total volume is then brought to 100 ml by means of orthodichlorobenzene. The autoclave is scavenged with nitrogen, then 200 bars of carbon monoxide are introduced. After isolating the reactor and starting the stirring, it is heated at 240° C. for 3 and three-quarter hours, thus limiting voluntarily the progress of the reaction. After cooling analysis shows that the O.C.R. of the nitrobenzene is 33.1%. The complex is purified by operating in the same way as in Example 10. Palladium tetraphenylporphyrin is thus obtained with a yield of 78%.

EXAMPLE 14

10 g of nitrobenzene, 0.6 g of tetraphenylporphyrin and 0.26 g of $RhCl_3.3H_2O$ are introduced into the autoclave. The total volume is brought to 100 ml with orthodichlorobenzene. It is scavenged with nitrogen and 200 bars of CO are introduced. The autoclave is isolated and while maintaining stirring, it is heated at 240° C. for 1 hour. After cooling, analysis shows that the O.C.R. of the nitrobenzene is 100% and the selectivity for phenylisocyanate is 46%. Azobenzene is not detected.

The isocyanate and the solvent are distilled and the residue is dissolved in the minimum volume of chloroform. The solution is chromatographied on a column filled with neutral alumina, then the solvent is evaporated. The residue is purified by continuous extraction with ethyl ether, which enables the rhodium tetraphenylporphyrin to be obtained with a yield of 83% with respect to the rhodium initially introduced.

What is claimed is:

1. A process for the synthesis of aromatic isocyanates which comprises reacting an aromatic mononitro derivative with carbon monoxide in the presence of a catalyst consisting of a metal complex of a porphyrin.

2. The process according to claims 1 in which the catalyst comprises a member selected from the group consisting of one or more porphyrins of metals belonging to Group VIII of the Periodic Classification of the Elements or one or more porphyrins of metals belonging to group $I_B$ of the Periodic Classification of the Elements and mixtures thereof.

3. The process according to claim 1 in which the porphyrin or porphyrins is or are substituted by a member selected from the group consisting of one or more of linear alkyl group containing from one to ten carbon atoms, branched alkyl group containing from one to ten carbon atoms, and aromatic group containing from six to twelve carbon atoms.

4. The process according to claim 1, 2 or 3 in which the catalyst is palladium tetraphenylporphyrin.

5. The process according to claim 1, 2 or 3 in which the catalyst is iron tetraphenylporphyrin.

6. The process according to claim 1, 2 or 3 in which the catalyst is an association of a porphyrin of a metal of Group $I_B$ and of a porphyrin of a metal of Group VIII of the Periodic Classification.

7. The process according to claim 6 in which the catalyst is deposited on a support selected from the group consisting of aluminas, silicas, silica-aluminas, active carbons, magnesia, zirconia and silicon carbide.

8. The process according to claim 5 in which the catalyst is deposited on a support selected form the group consisting of aluminas, silicas, silica-aluminas, active carbons, magnesia, zirconia and silicon carbide.

9. The process according to claim 4 in which the catalyst is deposited on a support selected from the group consisting of aluminas, silicas, silica-aluminas, active carbons, magnesia, zirconia and silicon carbide.

10. The process according to claim 3 in which the catalyst is deposited on a support selected from the group consisting of aluminas, silicas, silica-aluminas, active carbons, magnesia, zirconia and silicon carbide.

11. The process according to claim 2 in which the catalyst is deposited on a support selected from the group consisting of aluminas, silicas, silica-aluminas, active carbons, magnesia, zirconia and silicon carbide.

12. The process according to claim 1 in which the catalyst is deposited on a support selected from the group consisting of aluminas, silicas, silica-aluminas, active carbons, magnesia, zirconia and silicon carbide.

13. The process according to claim 1 in which the aromatic nitro derivative corresponds to the formula:

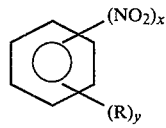

wherein $x=1$, $y=0$, 1, 2 or 3 and R represents a member selected from the group consisting of a halogen atom, an alkyl group having from 1 to 10 carbon atoms and an alkoxy group having from 1 to 10 carbon atoms.

14. The process according to claim 1, 2, 3 or 13 in which the nitro derivative is nitrobenzene.

15. The process according to claim 1, 2, 3 or 13 in which the reaction is brought into the liquid phase in the presence or absence of a solvent.

16. The process according to claim 15 in which the solvent is orthodichlorobenzene.

17. The process according to claim 1, 2, 3 or 13 wherein the ratio of the number of gram-atoms of metal to the number of nitro groups to be converted is between $10^{-4}$ and 1.

18. The process according to claim 17 wherein said ratio is between $5.10^{-3}$ and $10^{-1}$.

19. The process according to claim 1, 2, 3 or 13 wherein the reaction temperature is between 100° and 500° C.

20. The process according to claim 19 wherein the reaction temperature is between 150° and 300° C.

21. The process according to claim 1, 2, 3 or 13 wherein the reaction pressure is between 20 and 500 bars.

22. The process according to claim 21 wherein the reaction pressure is between 150 and 350 bars.

23. A process for the synthesis of aromatic isocyanates which comprises reacting an aromatic mononitro derivative with carbon monoxide in the presence of a catalyst consisting of a metallic porphyrin systhesized in situ from a porphyrin and a metal or a metal derivative.

24. The process according to claim 23 in which the metal or metal derivative is selected from the metals or derivatives of the metals of Group VIII and Group $I_B$ of the Periodic Classification of the Elements.

25. The process according to claim 23 in which the metal or metal derivative is palladium, rhodium or a derivative of said metals.

26. The process according to claim 23, 24 or 25 in which the metal derivative is an oxide or a salt.

27. The process according to claim 23 in which the metal derivative is palladium black or rhodium trichloride.

28. The process according to claim 27 in which the porphyrin is substituted by one or more linear or branched alkyl groups containing from one to ten carbon atoms, or by aromatic groups containing from six to twelve carbon atoms or by one or more acid chloride or amide groups.

29. The process according to claim 27 in which the porphyrin is tetraphenylporphyrin.

30. The process according to claim 23 in which the porphyrin is substituted by one or more linear or branched alkyl groups containing from one to ten carbon atoms, or by aromatic groups containing from six to twelve carbon atoms or by one or more acid chloride or amide groups.

31. The process according to claim 23 in which the porphyrin is tetraphenylporphyrin.

32. The process according to claim 23 in which palladium or rhodium tetraphenylporphyrin is synthesized in situ.

33. The process according to claim 23, 27, 28, 29, 30 or 31 in which the aromatic nitro derivative corresponds to the formula:

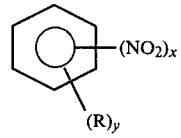

wherein $x=1$, $y=0$, 1, 2, 3 and R represents a member selected from the group consisting of a halogen atom, an alkyl group having from 1 to 10 carbon atoms or an alkoxy group having from 1 to 10 carbon atoms.

34. The process according to claim 33 in which the nitro derivative is nitrobenzene.

35. The process according to claim 33 in which the ratio of the number of gram-atoms of metal to the number of nitro groups to be converted is between $10^{-4}$ and 1.

36. The process according to claim 33 in which the reaction is carried out in the liquid phase in the presence or absence of a solvent.

37. The process according to claim 36 in which the solvent is orthodichlorobenzene.

38. The process according to claim 33 in which the reaction temperature is between 100° and 500° C.

39. The process according to claim 33 in which the reaction pressure is between 20 and 500 bars.

* * * * *